United States Patent [19]

Palmer et al.

[11] Patent Number: 5,113,015
[45] Date of Patent: May 12, 1992

[54] RECOVERY OF ACETIC ACID FROM METHYL ACETATE

[75] Inventors: David A. Palmer, Naperville; Keith D. Larson, Chicago; Kristi A. Fjare, Naperville, all of Ill.

[73] Assignee: Amoco Corporation, Chicago, Ill.

[21] Appl. No.: 616,213

[22] Filed: Nov. 20, 1990

[51] Int. Cl.⁵ .................. C07C 51/42; C07C 51/215; C07C 51/265
[52] U.S. Cl. .................. 562/608; 562/414; 562/485; 562/480; 203/DIG. 6
[58] Field of Search .................. 562/608, 414; 203/DIG. 6

[56] References Cited

U.S. PATENT DOCUMENTS

| | | | |
|---|---|---|---|
| 3,317,593 | 5/1967 | Enk et al. | 562/607 |
| 4,086,270 | 4/1978 | Wynkoop et al. | 562/484 |
| 4,232,177 | 11/1980 | Smith, Jr. | 203/28 |
| 4,307,254 | 12/1981 | Smith, Jr. | 203/DIG. 6 |
| 4,336,407 | 6/1982 | Smith, Jr. | 203/DIG. 6 |
| 4,978,807 | 12/1990 | Smith, Jr. | 568/694 |
| 4,982,022 | 1/1991 | Smith, Jr. et al. | 568/899 |

FOREIGN PATENT DOCUMENTS 0174344  10/1983  Japan .................. 562/608

*Primary Examiner*—Michael L. Shippen
*Assistant Examiner*—B. Frazier
*Attorney, Agent, or Firm*—Gunar J. Blumberg; William H. Magidson; Ralph C. Medhurst

[57] ABSTRACT

There is provided a process for recovering acetic acid from methyl acetate wherein the methyl acetate is hydrolyzed catalytically to methanol and acetic acid in the same tower or column that is used to separate the methanol from the acetic acid and the hydrolysis and separation are carried out coextensively in the vessel. The process is employed suitably in a process for the partial oxidation of a polymethylbenzene to a polycarboxylic acid in the presence of an oxidation catalyst and an acetic acid solvent.

40 Claims, 3 Drawing Sheets

RECOVERY OF ACETIC ACID FROM METHYL ACETATE

BACKGROUND OF THE INVENTION

Cross-Reference to Related Application

This application is being filed concurrently with U.S. Ser. No. 616,227, which is directed to a process for the conversion of a liquid organic material to a desired product, e.g., methyl acetate to acetic acid, by means of catalytic distillation employing a catalyst-packing material comprising a rigid, cellular monolith, e.g., a ceramic honeycomb monolith having its surface coated with silicalite.

Field of the Invention

The present invention relates to an improved method for handling the methyl acetate that is produced as a by-product during the oxidation of polymethylbenzenes to aromatic polycarboxylic acids. More particularly, the present invention relates to the hydrolysis of methyl acetate to methanol and acetic acid and the simultaneous separation of methanol and acetic acid.

Description of the Prior Art

Methyl acetate is a by-product obtained when polymethylbenzenes are oxidized to aromatic polycarboxylic acids. e.g., when p-xylene is oxidized to terephthalic acid. Much of the methyl acetate is lost due to its relatively high volatility. There is a definite economic incentive either to minimize methyl acetate production or to recover it as a useful product.

In U.S. Pat. No. 2,511,467, Gresham discloses passing a volatile aliphatic alcohol ester of an organic acid and water in the vapor phase over a metal salt of an organic acid corresponding to the organic acid of the ester being hydrolyzed at a temperature within the range of 250° C. (482° F.) to 400° C. (752° F.) to form the corresponding acid and alcohol, the metal of the salt being selected from cadmium, silver, and zinc. In the examples, methyl acetate is hydrolyzed over catalysts comprising zinc acetate or cadmium acetate.

In U.S. Pat. No. 2,719,166, Robertson, et al, disclose a process for the catalytic hydrolysis of esters in a mixture of organic compounds wherein the mixture is passed at a temperature of 25° C. (77° F.) to 260° C. (500° F.) over a hydrolysis catalyst comprising a high density, nuclear sulfonic-acid type cation-exchange resin having only one active exchange center in the resin and having a pH of 2 to 3.

In U.S. Pat. No. 2,936,321, Mercier discloses a continuous process wherein an ester of a lower alkanoic acid and a lower alkanol, such as methyl acetate, is hydrolyzed in the presence of water and a cation-exchange resin in its hydrogen form as a catalyst to produce a mixture of the acid (acetic acid), the alkanol (methanol), the ester (methyl acetate), and water, the mixture is withdrawn from the hydrolysis reactor and is distilled continuously in a single column having two sections, the ester is separated from water and alkanol at the top of the column by extractive water distillation, the aqueous alkanol is distilled to separate the ester as a head product and the ester is returned to the extractive distillation zone while the ester-free, aqueous alkanol is recovered, and substantially pure alkanoic acid is withdrawn from the base of the column.

In U.S. Pat. No. 3,317,593, Enk, et al, disclose a process for the hydrolysis of an alkanol derivative, such as an ester, in the presence of a cation exchanger in a reaction zone wherein the hydrolyte and water flow downwardly through a cation exchanger in the reaction zone at a temperature sufficient to vaporize the hydrolyte in the reaction zone and wherein the water-containing liquid hydrolysate flows downwardly through an extraction zone, the technique being such as to remove the reaction products while keeping the starting material, the hydrolyte, in the reaction zone. This permits the shift of the equilibrium in the direction of complete hydrolysis.

In U.S. Pat. No. 4,352,940, Adelman, et al, disclose the hydrolysis of methyl acetate in the presence of cation exchange resin wherein the effluent from the hydrolyzer is passed to a separator or flasher to separate at least a part of the unreacted methyl acetate with water overhead, optionally together with minor proportions of methanol and acetic acid, and this overhead fraction is recycled to the hydrolyzer while a mixture of acetic acid, methanol, water, and optionally methyl acetate is removed from the boiler of the separator or flasher and passed to other separation apparatus for the isolation of acetic acid and methanol.

In U.S. Pat. No. 4,435,595, Agreda, et al, disclose a reactive distillation process for the production of methyl acetate wherein approximately stoichiometric quantities of acetic acid and methanol are passed counter-currently through a single reactive distillation column in the presence of an acidic catalyst to produce methyl acetate. The acetic acid functions both as reactant and as extractive agent. Methyl acetate is removed from the top of the single column and water is removed continuously from the bottom of the column.

It has now been found that a hydrolysis catalyst, such as an acidic cation exchange resin, can be employed in a separation or distillation column or vessel in a manner that will enable the hydrolysis of the methyl acetate and the separation of the methanol from the acetic acid to occur coextensively in the vessel, i.e., simultaneously and in the same location in the vessel.

In U.S. Pat. No. 4,215,011, Smith, Jr, discloses a method for the separation of an isoolefin, preferably having four to six carbon atoms, from streams containing mixtures thereof with the corresponding normal olefins, wherein the mixture is fed into a reaction-distillation column containing a fixed-bed, acidic cation exchange resin to react the isoolefin with itself to form a dimer, and the dimer is separated from the normal olefin, the particulate catalytic material, i.e., the acidic cation exchange resin, being contained in a plurality of closed cloth pockets, which pockets are arranged and supported in the column by wire mesh.

In U.S. Pat. No. 4,443,559, Smith, Jr, discloses a catalytic distillation structure which comprises a catalyst component associated intimately with or surrounded by a resilient component, which is comprised of at least 70 vol % open space for providing a matrix of substantially open space. Examples of such resilient component are open-mesh, knitted, stainless wire (demister wire) or an expanded aluminum; open-mesh, knitted, polymeric filaments of nylon, Teflon, etc; and highly-open structure foamed material (reticulated polyurethane).

In a paper given in ACS Symposium Series No. 368 in Toronto, Ontario, Canada (Jun. 5-11, 1988) and printed in ACS Symposium Series No. 368, PERSPECTIVES IN MOLECULAR SIEVE SCIENCE, Flank and Whyte, Jr, Editors (1988), American Chemical Society. Patil, et al, show that a cordierite ceramic honeycomb washcoated with silicalite is suitable catalyst for methanol conversion.

The above catalytic distillation structures are suitable for use as catalyst-packing material in the processes of the present invention, wherein methyl acetate is hydrolyzed to acetic acid and methanol via catalytic distillation techniques.

SUMMARY OF THE INVENTION

There is provided a process for recovering acetic acid from methyl acetate wherein the methyl acetate is catalytically hydrolyzed to methanol and acetic acid in the same vessel or tower that is used to separate the methanol from the acetic acid and wherein the hydrolysis and separation are carried out coextensively in the vessel. The term "coextensively" is used herein to mean simultaneously and in the same location. There is provided also an improved process for the partial oxidation of a polymethylbenzene, such as para-xylene, in the presence of an oxidation catalyst and a solvent comprising acetic acid to an aromatic polycarboxylic acid, such as terephthalic acid, wherein the methyl acetate by-product from the oxidation process is catalytically hydrolyzed to acetic acid and methanol and the acetic acid is separated from the methanol in the same vessel that contains the hydrolysis catalyst, the hydrolysis and separation being carried out coextensively. A preferred embodiment employs an acetic acid dehydration tower or column as the vessel containing the hydrolysis catalyst. A typical hydrolysis catalyst for use in these processes is an acidic cation exchange resin, such as a sulfonated polystyrene with divinyl benzene crosslinking.

BRIEF DESCRIPTION OF THE DRAWINGS

Five figures are appended hereto, which figures are simplified diagrams directed to either a catalytic distillation operation or processes for the oxidation of a para-xylene feed to terephthalic acid. Various pieces of auxiliary equipment, such as pumps, blowers, and heat exchangers, are not shown. However, one skilled in the art would recognize easily where such equipment would be located and when they would be used.

DESCRIPTION AND PREFERRED EMBODIMENTS

As pointed out hereinabove, acetic acid can be recovered from methyl acetate typically by the catalytic hydrolysis of the methyl acetate to form methanol and acetic acid and by subsequently separating acetic acid from the methanol either in a separate separation vessel that is not the same as the vessel containing the hydrolysis catalyst or in a separate section of the same vessel.

Now there has been shown a process wherein methyl acetate is hydrolyzed to acetic acid and methanol and wherein the acetic acid is separated from the methanol in the same vessel containing the hydrolysis catalyst, hydrolysis and separation being conducted coextensively in the same vessel.

According to the present invention, there is provided a process for recovering acetic acid from methyl acetate, which process comprises contacting in a separation vessel a stream comprising methyl acetate with water in the presence of a catalyst-packing material comprising a hydrolysis catalyst and a solvent comprising acetic acid to produce methanol and acetic acid, separating said methanol from said acetic acid in said separation vessel, said contacting and said separating being conducted coextensively, and recovering said acetic acid.

Such a process can be used conveniently to recover acetic acid from the methyl acetate by-product produced during the partial oxidation of a polymethylbenzene, such as para-xylene, to an aromatic polycarboxylic acid, such as terephthalic acid. In doing this, it can improve the economics of the oxidation process. There is a definite economic incentive for either minimizing the production of the volatile methyl acetate by-product or recovering it as a useful product.

According to the present invention, there is provided also a process for the partial oxidation of a polymethylbenzene to the corresponding aromatic polycarboxylic acid, which process comprises contacting a feed comprising said polymethylbenzene with molecular oxygen in a reaction zone in the presence of an oxidation catalyst and a solvent comprising acetic acid to produce said polycarboxylic acid and at least a small amount of methyl acetate, withdrawing from said reaction zone said polycarboxylic acid and a first stream comprising said methyl acetate, water, and acetic acid, introducing said first stream into a dehydration column wherein a second stream comprising water and methyl acetate is separated from a third stream comprising acetic acid, contacting said second stream comprising methyl acetate with water in a separation column containing a catalyst-packing material comprising a hydrolysis catalyst to hydrolyze said methyl acetate into methanol and acetic acid product, separating said methanol from said acetic acid product in said separation column, said contacting and said separating being carried out coextensively in said separation column, and sending at least a large portion of said acetic acid product to said reaction zone. It is contemplated that at least 80 percent of the acetic acid produced in the separation column will be recovered and sent to the reaction zone. It is believed that essentially all of the methyl acetate can be reacted at one time, accompanied by continuous separation of the products, methanol and acetic acid.

The processes of the present invention employ the unit operation that is referred to as "Catalytic Distillation." In catalytic distillation, a section of a distillation unit is used to carry out simultaneously reaction and separation. As a result, equilibrium-limited reactions may be conducted without the use of recycle streams. The catalyst, also hereinafter referred to as catalyst-packing material, serves as packing and is installed in the distillation column in such a way that there is sufficient open area for gas and liquid flow. The reaction zone can be operated continuously in either a gas phase or a liquid phase. Moderately equilibrium-limited reactions can be carried to completion. Capital cost may be reduced by as much as 50%. Since most reactions are exothermic, there is a reduction of reboiler duty. Continuous phase equilibria eliminate overheating and hot spots. Continuous washing of the catalyst with liquid prolongs the catalyst life.

It is shown hereinafter that a catalyst-packing material comprising a hydrolysis catalyst, e.g., a strongly acidic cation exchange resin, can be used conveniently as the catalyst in an embodiment of the process of the present invention, i.e., for hydrolyzing methyl acetate to acetic acid and methanol in a separation vessel. In such an installation, the catalytic material is wrapped in fiberglass and the resulting mat is rolled up with wire mesh between the layers to promote fluid flow. Many bales of catalyst are employed. At each level, the bales are arranged to cover the open area from the stack at the level below. This type of catalyst-packing material is discussed in U.S. Pat. No. 4,215,011, which is incorporated herein by reference.

A catalyst-packing material comprising, a catalyst component associated intimately with or surrounded by a resilient component, which is comprised of at least 70 vol % open space for providing a matrix of substantially open space, is disclosed in U.S. Pat. No. 4,443,559. The resilient component may be open-mesh, knitted stainless wire or open-mesh, knitted polymeric filaments of nylon, Teflon, and the like. U.S. Pat. No. 4,443,559 is incorporated herein by reference.

Another material that may be used as catalyst-packing material in processes employing catalytic distillation is a rigid, cellular monolith, as disclosed in concurrently-filed patent application U.S. Ser. No. 616,227, which is incorporated herein by reference. It is contemplated that the structure of such rigid, cellular monoliths has a cell density that is at least about 5 cells per sq in and a surface area that is consistent with a low pressure drop. As cell density increases, surface area increases.

Typically, cell density will fall within the range of about 5 cells per sq in to about 1,000 cells per sq in; preferably, within the range of about 9 cells per sq in to about 400 cells per sq in; and more preferably, within the range of about 100 cells per sq in to about 200 cells per sq in.

The monolith can be fabricated from various materials, e.g., steel, polymers of various types, and ceramic materials. In addition, it can be made from corrugated sheets of metal or plastics or ceramics. Such materials may be obtained from Koch Engineering under the names of FLEXIPAC and FLEXERAMIC.

Depending upon the application, the rigid, cellular monolith may have coated on its surface a catalytic amount of a catalytic material, such as phosphoric acid, sulfuric acid, silicalite, or an acidic cation exchange resin. The term "catalytic amount" is used herein to indicate that the amount is sufficient to catalyze the reaction for which the catalytic material is being used. Typically, the amount will be within the range of about 0 wt % to about 10 wt %, based on the total weight of the composition. Preferably, the amount will be within the range of about a trace to about 5 wt %, based on the total weight of the composition.

A suitable rigid, cellular monolith is a ceramic honeycomb monolith. Typical ceramic honeycomb monoliths are manufactured by the Corning Company under the brand name of "Celcor." Such monoliths are produced with cell densities of 9, 16, 25, 50, 100, 200, 300, and 400 cells per sq in. The length is typically five or six inches long. The Celcor products are made from cordierite ($2 MgO \cdot 2Al_2O_3 \cdot 5SiO_2$), mullite ($3Al_2O_3 \cdot SiO_2$), and cordierite-mullite. These, as well as other suitable ceramic monoliths, may be used in the preparation of catalyst-packing material for use in the separation vessels of the present invention. However, it is contemplated that other rigid materials are suitable for use as such catalyst-packing material.

The honeycomb-type monoliths can be prepared from materials other than cordierite and mullite. For example, they can be made of alumina, silica-alumina, or molecular sieves. Cordierite is a preferred material. It is a neutral material. Alumina is weakly acidic. Both silica-alumina and molecular sieves are acidic.

Cordierite is a typical rigid, ceramic, honeycomb monolith. It is partially porous and has a surface area that falls within the range of about 23 sq ft per cu ft to about 70 sq ft per cu ft. Its cell structure has cell sizes ranging from about 50 cells per square inch to about 400 cells per square inch.

This catalyst-packing material furnishes a particularly advantageous configuration. Each channel is vertical and provides considerable area for vapor-liquid equilibrium. As the reaction proceeds in the catalytic zone, the heat generated by the reaction is consumed efficiently via vaporization of the downflowing reflux.

For the recovery of acetic acid from methyl acetate, a preferred catalyst is one comprising silicalite or cordierite.

When the catalyst becomes deactivated, it can be reactivated by treatment in air or other oxygen-containing gas at a temperature within the range of about 371° C. (700° F.) to about 538° C. (1,000° F.).

Numerous aromatic polycarboxylic acids may be prepared conveniently by the catalytic oxidation of alkyl-substituted aryl compounds via molecular oxygen. Such oxidation is effected by reacting the alkyl-substituted aryl compound with molecular oxygen in the conjoint presence of catalytic amounts of a heavy metal catalyst and of bromine. The heavy metal catalyst comprises a member of the group consisting of manganese, cobalt, nickel, chromium, vanadium, molybdenum, tungsten, tin, cerium, and mixtures thereof. These metals, as well as others that have atomic numbers that are not greater than 84, are suitable for this oxidation catalyst and are presented in the "Periodic Chart of the Elements" on pages 58 and 59 of LANGE'S HANDBOOK OF CHEMISTRY, 6th edition, published by Handbook Publishers, Inc., Sandusky, Ohio, 1946. A preferred heavy metal catalyst comprises manganese and cobalt. The metal of the oxidation catalyst may be added in the elemental, combined, or ionic from. In addition, the bromine of the oxidation catalyst may be added in the elemental, combined, or ionic form. The metal or metals may be supplied in the form of metal salts of a lower aliphatic carboxylic acid, such as a metal acetate, in the form of an organic complex, such as an acetylacetonate, or as metal salts, such as the borates, halides, and nitrates. Bromine may be added as ionic bromine, such as ammonium bromide or other bromine compound that is soluble in the reaction medium. Potassium bromide, tetrabromoethane, and benzyl bromide are suitable sources of bromine.

The oxidation reaction is conducted at a temperature within the range of about 120° C. (248° F.) to about 275° C. (527° F.), desirably within the range of about 150° C. (302° F.) to about 250° C. (482° F.), and preferably within the range of about 170° C. (338° F.) to about 225° C. (437° F.). It is carried out under essentially liquid-phase conditions. The temperature and pressure should be so regulated as to provide a liquid phase in the reaction zone. Generally, the pressure is maintained within the range of atmospheric to about 1,500 psig (10,444 kPa).

The oxidation is carried out with an oxygen-containing gas as a source of molecular oxygen. The gas may be 100% oxygen or a gas mixture containing a lower concentration of oxygen, e.g., air.

The reaction time should be sufficiently long to enable a suitable conversion to result, i.e., about 0.5 to about 25 hours or more. A reaction time within the range of about 0.5 hour to about 4 hours is preferred.

Typically, oxygen is used in an amount to provide a mole ratio of about 2 moles of oxygen per mole of substituted aromatic material to about 500 moles of oxygen per mole of substituted aromatic material; desirably, within the range of about 5 to about 300 moles of oxygen per mole of substituted aromatic material; and preferably, within the range of about 5 to about 75 moles of oxygen per mole of substituted aromatic material.

The oxidation is a liquid-phase reaction. The liquid phase may comprise all or a portion of the organic reactant, or it may comprise a reaction medium in which the organic reactant is soluble or suspended. Such reaction medium may be added to facilitate carrying out the desired reaction or recovering desired product(s). This added reaction medium is suitably a monocarboxylic acid relatively stable or inert to oxidation in the reaction system. Typically, the monocarboxylic acid contains 1 to 8 carbon atoms per molecule. Preferably, the acid contains 2 to 4 carbon atoms, e.g., acetic acid.

Suitably, the reaction medium, if a lower aliphatic monocarboxylic acid, is used in an amount to provide a ratio of about 0.1 to about 10 parts by weight reaction medium per part of aromatic material, desirably a ratio of about 0.5 to about 4, and preferably a ratio of about 1 to about 2.5 parts by weight reaction medium per part of aromatic material.

In U.S. Pat. Nos. 2,833,816, 3,089,906, and 3,089,907, Saffer, et al, teach various embodiments of the above-described process. In U.S. Pat. No. 4,053,506, Park, et al, provide a process for producing terephthalic acid or isophthalic acid of fiber-grade quality.

Figure 1:
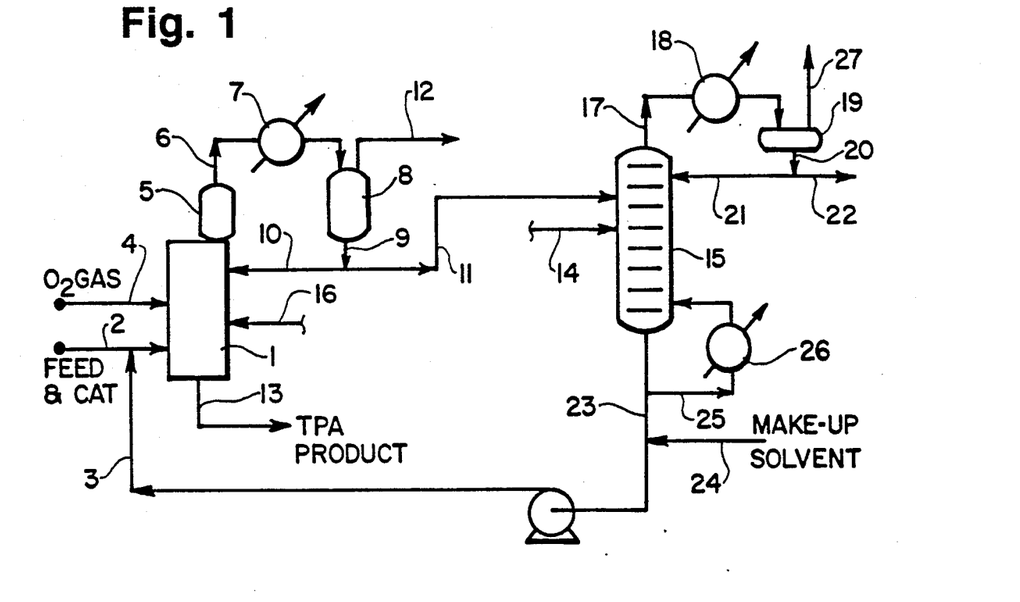
FIG. 1 is a simplified schematic diagram of a typical process for the partial catalytic oxidation of para-xylene to terephthalic acid.

A simplified process scheme of a typical xylene oxidation process is presented in the accompanying FIG. 1. In this process, the xylene feed and catalyst are introduced into the reaction (oxidation) zone 1 through line 2 after the feed and catalyst have been combined with recycled solvent from line 3. An oxygen-containing gas, such as compressed air, is introduced into reaction zone 1 via line 4. The reaction mixture is stirred or agitated continuously in reaction zone 1, which may exist in the form of one or more reactors or stages. A portion of the reaction zone overhead condensate, which is rich in water, is removed to control effectively the water concentration in the reaction zone 1. Vapors from the reaction zone 1 pass through a primary water cooled reflux condenser 5. A large portion of the acetic acid solvent contained in the overhead vapor is condensed and removed as liquid reflux to reaction zone 1. Uncondensed vapors pass through line 6 and heat exchanger 7. Additional vapor is condensed and the condensate is collected in a secondary condenser pot 8. The condensate, which contains water-rich acetic acid, is withdrawn from condenser pot 8 through line 9 to be split into two streams, one of which is returned to reaction zone 1 via line 10 and one of which is passed to solvent recovery through line 11. Any vapor remaining in condenser pot 8 is vented through line 12.

The oxidation catalyst system employed in this process scheme is similar to the ones described hereinabove, and the process conditions utilized in this process scheme fall within the ranges of values presented hereinabove.

The terephthalic acid (TPA) product is removed from reaction zone 1 as fluid oxidation effluent by way of line 13 and is sent to a recovery and purification system (not shown). A suitable recovery and purification system is disclosed in U.S. Pat. No. 4,053,506 by Park, et al.

The condensate in line 11 and solvent vapors obtained from the recovery and purification system in line 14 are charged to distillation column 15 for recovery of acetic acid. In addition, solvent from the recovery and purification system is introduced into reaction zone 1 via line 16. Water vapor is removed from column 15 via line 17 through heat exchanger 18. The resulting condensate is collected in condensate drum 19. This condensate is removed from drum 19 through line 20 and is split into two streams, one of which passes through line 21 as reflux to column 15 and one of which is removed in line 22 as discard.

Recovered acetic acid solvent is withdrawn from column 15 through line 23 and is combined with make-up fresh acetic acid from line 24. A portion of its recovered acetic acid is passed through line 25 and heat exchanger 26 into the bottom of column 15. The acetic acid stream is then passed through line 3 to be combined with the xylene feed and catalyst in line 2, as mentioned hereinabove. Remaining vapor is removed from drum 19 via line 27.

A volatile by-product that is formed during the oxidation of polymethylbenzenes in the presence of an acetic acid solvent is methyl acetate. It results from the degradation of acetic acid to methanol and carbon oxides. The methanol tends to esterify with acetic acid to produce the methyl acetate. Since methyl acetate is very volatile, much of it is lost from the process in the tower wherein water is separated from acetic acid. There is a potential economic advantage for the oxidation process if a sufficient amount of the methyl acetate is recovered.

Various methods for recovery of the methyl acetate have been considered. The methyl acetate could be recovered by compression of the vapor stream out of the condensate drum connected to the distillation tower employed to separate acetic acid from water. Unfortunately, prohibitive pressures and refrigeration would be required to obtain high recoveries via this technique in view of the high volume of inerts in this vapor stream. In another method, recycle of the methyl acetate to the oxidation reactors can provide recovery of acetic acid by shifting the hydrolysis equilibrium to regain acetic acid. However, it may be difficult to recover methyl acetate in sufficient quantities to maintain the concentration of methyl acetate in the reactor solvent necessary to minimize methyl acetate formation. As shown hereinabove in the prior art, liquid or gas phase catalytic hydrolysis of methyl acetate to acetic acid followed by separation techniques to separate acetic acid from methanol is known.

Now another method has been found. In this method, a stream containing methyl acetate is contacted with a catalyst in a vertical distillation tower or column to catalytically hydrolyze the methyl acetate to acetic acid and methanol, and the tower may be the same tower that is used to separate the acetic acid from the methanol. A suitable catalyst for use in this catalytic distillation technique is an acidic cation exchange resin.

Figure 2:
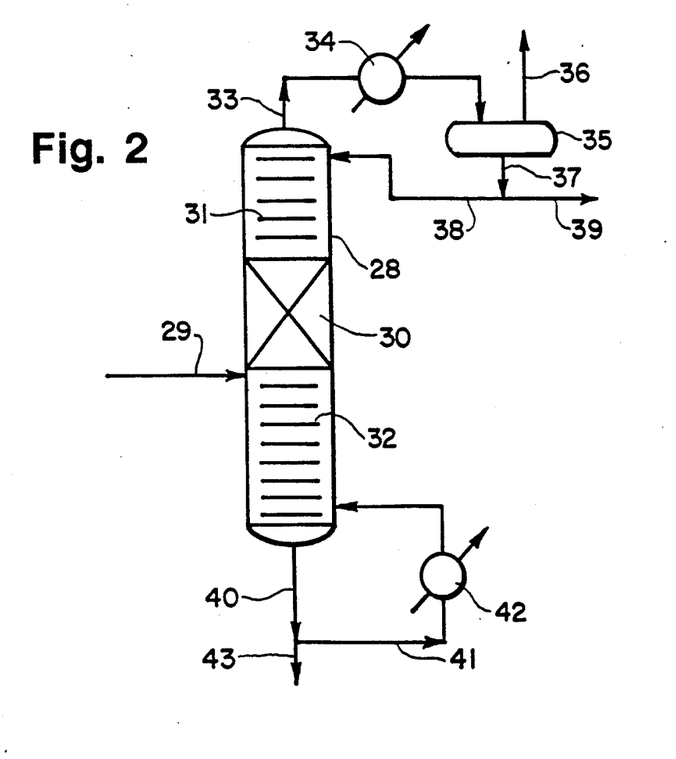
FIG. 2 is a simplified diagram of a typical catalytic distillation installation.

The accompanying FIG. 2 is a simplified diagram of a typical catalytic distillation installation.

Referring to FIG. 2, column 28 is a vertical distillation column. A feed stream comprising a liquid organic material is introduced into column 28 via line 29. Column 28 contains catalyst zone 30, which contains catalyst-packing material, which may be present in the form of one or more beds. The catalyst-packing material is that material which will catalyze the conversion of the liquid organic material passing through catalyst zone 30.

As represented in FIG. 2, the feed stream is introduced into column 28 at a point below catalyst zone 30. Depending upon the reaction occurring in the catalyst zone, the feed may be introduced into the column at a point in the catalyst zone, at a point above the catalyst zone, or at a point below the catalyst zone.

The column may have trays above the catalyst zone, as shown by upper zone 31, and/or trays below the catalyst zone, as represented by lower zone 32. Alternatively, suitable conventional packing, such as Rashig rings, Pall rings, or saddles, may be used in place of trays in either the upper zone 31 or the lower zone 32.

At least a portion of the liquid organic material is converted to the desired product in catalyst zone 30 while concurrently this heavier product is separated from the lighter material in column 28. The lighter and non-condensable material pass up through the upper zone 31 and out of column 28 via line 33. The product and other heavier material pass down through the column through lower zone 32.

The lighter and non-condensable materials pass through line 33 and condenser 34 into condensate drum 35 where the condensed material is separated from the non-condensables. The non-condensables are removed from the system by way of line 36. The condensed material is passed from condensate drum 35 by way of line 37, a portion of the condensed material being returned to column 28 via line 38 as reflux and, if needed, a portion being withdrawn from the system via line 39.

The heavier material, i.e., the higher-boiling material, in column 28 is passed from lower zone 32 out of column 28 by way of line 40. A portion of the material in line 40 is passed through line 41 and reboiler 42 into column 28. Product is removed from the system via line 43.

While there are several streams in a process for the oxidation of polymethylbenzenes to polycarboxylic acids that are capable of being treated by catalytic distillation to recover acetic acid, e.g., the water withdrawal stream off of the oxidation reactor condenser, the vent from the tower employed to separate water from acetic acid, and bottoms from the scrubber for polymethylbenzenes, the most suitable stream is the vent stream from the tower separating water from acetic acid, i.e., the acetic acid dehydration tower. It appears that the largest portion of methyl acetate is lost from the oxidation process via this stream.

It is to be understood that while the following discussion is directed to employing the catalytic distillation technique to treat the vent stream from the acetic acid dehydration tower, it can be used in any of the streams mentioned hereinabove to recover the acetic acid value in that stream.

Figure 3:
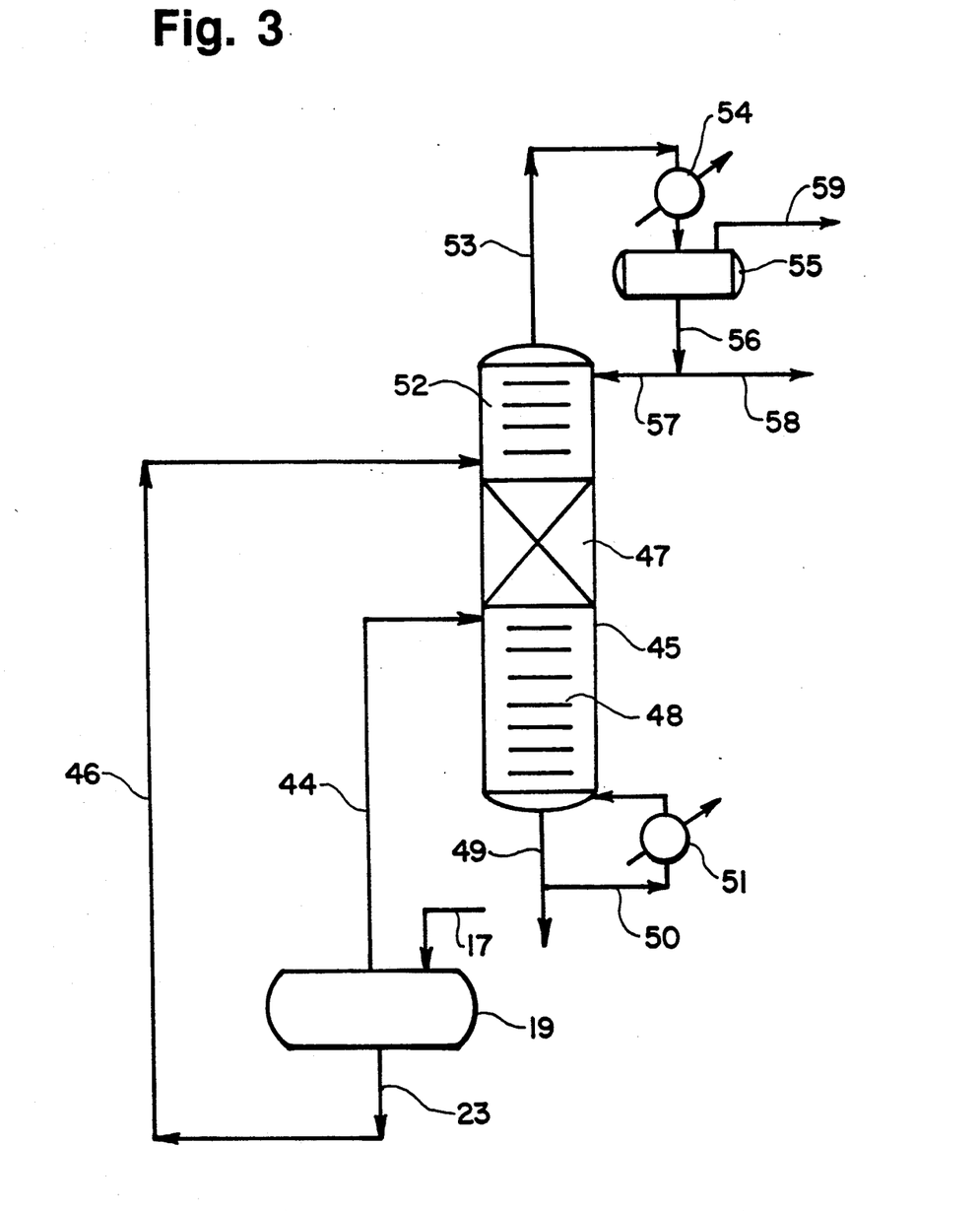
FIG. 3 is a simplified diagram showing how the process of the present invention is used to recover acetic acid from the methyl acetate produced in a process for oxidizing para-xylene to terephthalic acid when using a combination hydrolysis separation tower.

FIG. 3 depicts the technique for recovering acetic acid from methyl acetate according to the present invention. The technique employs a separation tower containing a catalyst-packing material comprising a suitable hydrolysis catalyst, the contacting of the stream containing methyl acetate with the catalyst-packing material and the separation of the resulting methanol and acetic acid being carried out coextensively in the separation tower. This technique may be used to treat any stream containing methyl acetate. In FIG. 3, it is being employed to treat the cooled overhead stream from distillation tower 15 of FIG. 1, which cooled overhead stream is introduced into condensate drum 19 via line 17. In drum 19, vapor is separated from liquid condensate. The high volatility of the methyl acetate in the overhead stream results in the concentration of 95% of the methyl acetate being in the vapor phase. This vapor, which contains methyl acetate, water, and inert gases, is passed through line 44 into separation tower 45, where it contacts counter-currently a stream of liquid condensate from line 46. The liquid condensate is withdrawn from drum 19 via line 23 and is passed through line 46 to the top section 52 of tower 45. Tower 45 is packed with a hydrolysis catalyst. Suitably, the hydrolysis catalyst, an acidic cation exchange resin, is placed in pockets in a fiber glass cloth belt, which is then rolled into cylindrical bales, 8 to 14 inches in diameter and 20 inches in length. This packed area of tower 45 is identified as packing 47. In tower 45, the methyl acetate is converted to acetic acid and methanol. The less volatile acetic acid is retained in the bottoms stream, which is passed down through lower tray zone 48 and withdrawn from column or tower 45 via line 49. A portion of this stream in line 49 is passed through line 50 and reboiler 51 to be returned to tower 45, while the remainder in line 49 is recycled to the appropriate tray of the acetic acid dehydration tower (distillation column) (not shown in FIG. 3). The more volatile methanol is carried up through upper tray zone 52 and out of tower 45 by way of line 53. The stream in line 53 is cooled in condenser 54 and the condensed material is separated from non-condensables in condensate drum 55. The condensed material, containing methanol, is removed from drum 55 by way of line 56. A portion of the condensed material is passed through line 57 into tower 45 as reflux, while the remainder is removed from the system by way of line 58. The non-condensables and methanol are withdrawn via line 59.

Figure 4:
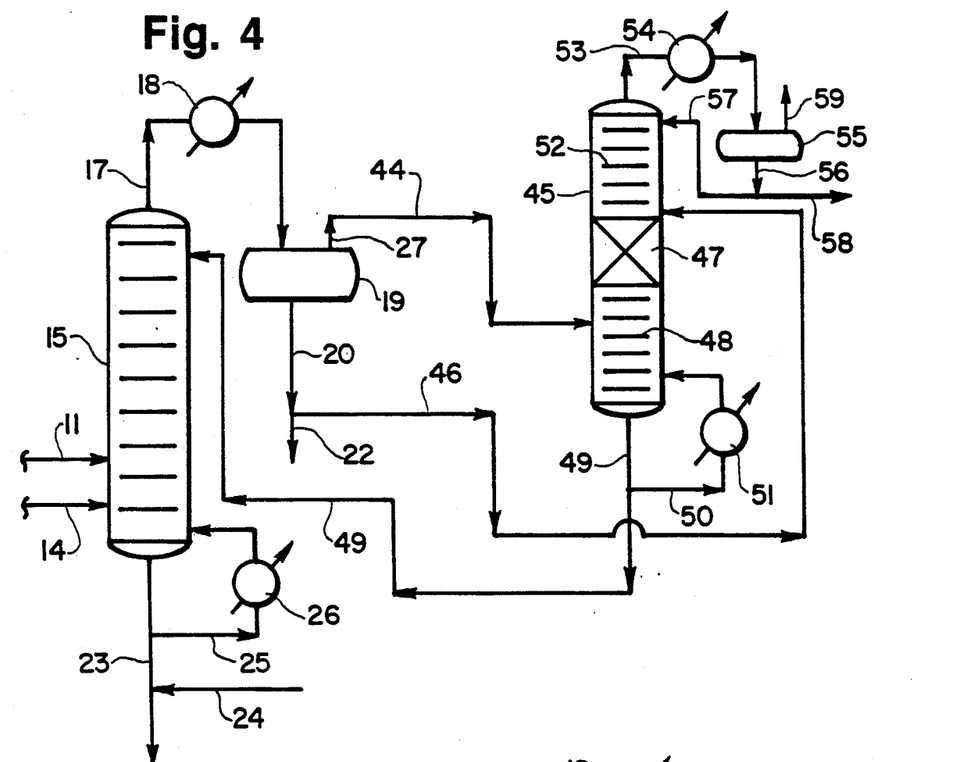
FIG. 4 is a simplified schematic diagram of the process demonstrated in FIG. 3 being utilized in the oxidation process presented in FIG. 1.

FIG. 4 represents a process scheme wherein the methyl acetate recovery scheme presented in FIG. 3 is applied to the acetic acid dehydration tower 15 of the process system represented in FIG. 1. Accordingly, the water-rich acetic acid condensate in line 11 is sent to dehydration tower 15. The solvent vapors obtained from the recovery and purification system are introduced into tower 15 via line 14. Water vapor is removed from column 15 via line 17 through heat exchanger 18. The resulting condensate is collected in condensate drum 19 and is withdrawn from drum 19 through line 20. The condensate is split into two streams, one of which passes through line 46 to column 45 and one of which is withdrawn through line 22 as discard. Column 45 is packed with acidic cation exchange resin. The condensate from line 46 passes down through the bed(s)

of cation exchange resin in column 47 where it contacts vapor from line 44, which vapor originated in condensate drum 19 and which vapor is passed through line 27 and line 44 and is introduced into column 45 below the cation exchange resin. The methyl acetate is hydrolyzed to acetic acid and methanol in catalyst zone 47 in column 45. The column 45 acts as a separator to separate methanol from the acetic acid. Acetic acid is passed down through lower tray zone 48 and out of column 45 via line 49 and is passed through line 49 into dehydration tower 15. Methanol and non-condensables are passed up through upper tray zone 52 and out of column 45 by way of line 53. Methanol and non-condensables are passed through line 53 and condenser 54 to condensate drum 55, where the condensed material containing methanol is separated from the non-condensables. The condensed material is withdrawn from condensate drum 55 by way of line 56. A portion of the condensed material is returned to column 45 as reflux via line 57, while a second portion is passed through line 58. Methanol is recovered from drum 55 via lines 58 and 59. The acetic acid is withdrawn from column 45 via line 49 to be recycled to dehydration column 15. Acetic acid is withdrawn from dehydration column 15 through line 23. A portion of the recovered acetic acid in line 23 is passed through line 25 and reboiler 26 into the bottom of column 15. The remainder of the recovered acetic acid is augmented with make-up acetic acid from line 24, when needed, and recycled to the oxidation reaction zone (not shown in FIG. 4).

In the above embodiment of the present invention, catalytic distillation enables the hydrolysis of methyl acetate and the separation of the products to be carried out coextensively in the same vessel.

In a second embodiment of the present invention, the catalyst for the hydrolysis is placed inside the acetic acid dehydration tower of the oxidation process and catalytic distillation is conducted in that tower. This embodiment is depicted in FIG. 5.

Figure 5:
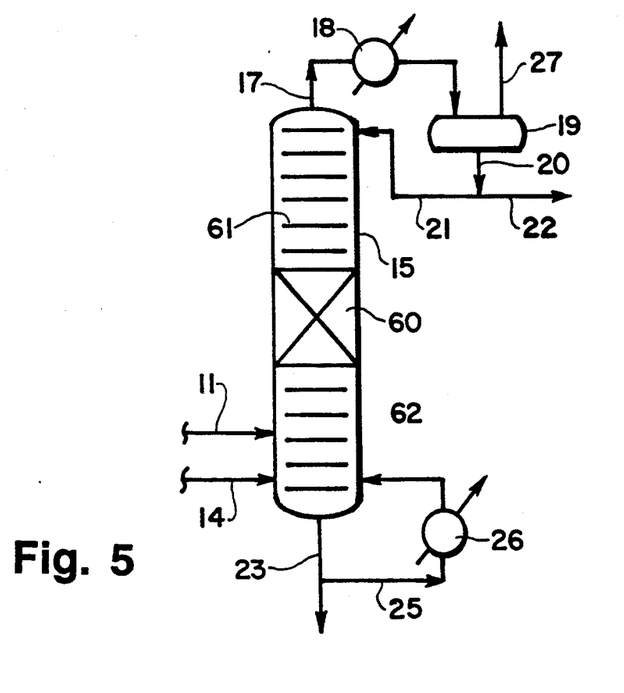
FIG. 5 is a simplified diagram which depicts an embodiment of the process of the present invention wherein the acetic acid dehydration tower of the terephthalic acid process of FIG. 1 is used as a hydrolysis tower.

Referring to FIG. 5, the condensate in line 11 and solvent vapors obtained from the recovery and purification system in line 14 are charged to distillation tower 15 for recovery of acetic acid. Water vapor is removed from tower 15 via line 17 through heat exchanger 18. The resulting cooled overhead stream is passed into condensate drum 19 via line 17. Remaining vapor is removed from drum 19 via line 27, while condensate is withdrawn from drum 19 through line 20 and is split into two streams. One of these streams passes through line 21 as reflux to column or tower 15 and the other is removed in line 22 as discard.

Hydrolysis catalyst is located in tower 15 in the section identified as 60. Consequently, the methyl acetate, as it rises through tower 15, is contacted counter-currently in the presence of hydrolysis catalyst with the condensate from condensate drum 19 as the condensate is passed down through the upper tray zone 61 and catalyst zone 60 in tower 15. The methyl acetate is hydrolyzed to acetic acid and methanol in catalyst zone 60. Acetic acid is passed down through lower tray zone 62 in tower 15. The methanol, which is carried out of tower 15 in the vapor stream via line 17 is recovered through lines 22 and 27. The acetic acid is withdrawn from tower 15 via line 23 for use as solvent in the oxidation process. A portion of the stream in line 23 is passed through line 25 and reboiler 26 and introduced into the bottom of tower 15.

In the system or design of these embodiments, the hydrolysis reaction is allowed to go to completion, the heat of reaction would be absorbed easily, and the catalyst packing serves simultaneously as a separation medium.

If the process of recovering acetic acid from methyl acetate of the present invention is employed in the acetic acid dehydration tower of an existing plant, the acetic acid is produced wherein it can be separated readily from the water, an extra column with associated hardware becomes unnecessary for methyl acetate recovery, and the only cost required is that of the catalyst and tray modifications to a small section of the tower.

The hydrolysis catalyst, i.e., the catalyst-packing material, may be typically a strongly acidic cation exchange resin. An appropriate catalyst is a sulfonated polystyrene with divinylbenzene crosslinking. Such resin catalyst can be obtained commercially from Rohm and Haas as Amberlyst 15 and from Dow Chemical Company as Dowex 50X2. Amberlyst 15 is a sulfonated styrene-divinylbenzene copolymer and has the form of macroreticular beads.

A preferred catalyst-packing material for use in the process schemes of FIGS. 4 and 5 has now been found. This catalyst-packing material is a rigid, cellular monolith, such as a ceramic honeycomb monolith having coated on its surface an acidic catalyst material, such as the molecular sieve silicalite. As noted hereinabove, this catalyst-packing material may be obtained from the Corning Company.

The column that is used to recover the acetic acid from the methyl acetate is operated at a pressure that may be sub-atmospheric, atmospheric, or above-atmospheric pressure. Typically, the pressure will fall within the range of about 1.3 psia (8.96 kPa) to about 600 psia (4,137 kPa). Preferably, the pressure will be within the range of about atmospheric to about 150 psia (1,034 kPa).

The column containing the hydrolysis catalyst is operated at a liquid volumetric hourly space velocity (SV) within the range of about 0.1 $hr^{-1}$ to about 10 $hr^{-1}$, preferably within the range of about 0.5 $hr^{-1}$ to about 5 $hr^{-1}$.

The temperatures in the column depend upon the composition and pressure. Since both the composition of material and the pressure change throughout the column, the temperature at a certain location in the column is dictated by the composition and pressure at that location. Hence, the temperature could be less than 37.8° C. (100° F.) and as high as 298° C. (568° F.) in a certain location in the column. These temperature values are presented for purposes of illustration only and are not given to provide a specific temperature range of values.

In the case of employing an existing dehydration column in an existing unit as the column for recovering acetic acid from methyl acetate, more than likely the column will be operated at a pressure that is near atmospheric pressure.

The following examples are being presented to facilitate an understanding of the present invention. They are being presented for the purpose of illustration and are not intended to limit the scope of the present invention.

EXAMPLE I

The process of the present invention was simulated by means of FRACHEM, a computer program for simulating reactive distillations. The results of this simulation are presented in Table I hereinbelow. Six equilibrium stages (vapor-liquid and reaction equilibrium obtained in each stage) of packing were found to be adequate to recover 95% of the acetic acid content of the dehydration tower vent. Only 7% of the methyl acetate was recovered as methyl acetate, the rest of the methyl acetate being converted to acetic acid. The ratio of condensate reflux to feed was approximately 0.8 on an inert-free basis. Equilibrium data for the model was obtained from an Amoco Chemical Company study of the hydrolysis of methyl acetate. For simplification, all of the inerts from secondary oxidation (nitrogen, oxygen, carbon monoxide, and carbon dioxide) were assumed to behave as nitrogen, the primary component.

The results of this computer simulation of the process of the present invention to recover acetic acid from the hydrolysis of methyl acetate indicate its feasibility.

TABLE I

FRACHEM SIMULATION OF CATALYTIC DISTILLATION - SELECTED OUTPUT

Feed Summary

| | Feed 1<br>lb-mole/hr<br>Tray No. 1 | Feed 2<br>lb-mole/hr<br>Tray no. 6 |
|---|---|---|
| Water | 93.9000 | 80.0000 |
| Acetic acid | 0.3160 | 0.2700 |
| Methyl acetate | 9.5500 | 0.0800 |
| Methanol | 0.0000 | 0.0000 |
| Nitrogen | 433.0000 | 0.0000 |
| Total feed, lb mol/hr | 536.7659 | 80.3500 |
| Feed Temp. °F. | 180.00 | 180.00 |
| °C. | 82.2222 | 82.2222 |
| Feed Pressure, psia | 14.7 | 14.7 |

Product Summary
Vapor Distillate from Stage 6

| Component | lb-mole/hr | Composition,<br>mole % |
|---|---|---|
| Water | 95.22079 | 17.71216 |
| Acetic acid | 1.378165 | 0.2563547 |
| Methyl acetate | 0.2457804 | 0.4571800 E − 01 |
| Methanol | 7.849677 | 1.460131 |
| Nitrogen | 432.9065 | 80.52563 |
| Total | 537.6008 | 100.0000 |
| Temp. °F. | 137.3822 | |
| °C. | 58.5457 | |
| Pressure, psia | 14.70000 | |
| Vapor fraction | 1.000000 | |

Liquid Product from Bottom Stage 1

| Component | lb-mole/hr | Composition<br>mole % |
|---|---|---|
| Water | 69.87082 | 87.87067 |
| Acetic acid | 8.016143 | 10.08123 |
| Methyl acetate | 0.5759060 | 0.7242687 |
| Methanol | 0.9586316 | 1.205590 |
| Nitrogen | 0.9406072 E − 01 | 0.1182922 |
| Total | 79.51552 | 100.0000 |
| Temp. °F. | 139.3994 | |
| °C. | 59.6663 | |
| Pressure, psia | 14.7 | |
| Vapor fraction | 0.0000000 E + 00 | |

Liquid Rate of Disappearance, lb-mole

| Stage No. | Water | Acetic Acid | Methyl Acetate | Methanol | Nitrogen |
|---|---|---|---|---|---|
| 6 | 0.204 | −0.204 | 0.204 | −0.204 | 0.000 E + 00 |

TABLE I-continued

FRACHEM SIMULATION OF CATALYTIC DISTILLATION - SELECTED OUTPUT

| 5 | 0.284 | −0.284 | 0.284 | −0.284 | 0.000 E − 00 |
| 4 | 0.499 | −0.499 | 0.499 | −0.499 | 0.000 E − 00 |
| 3 | 0.933 | −0.933 | 0.933 | −0.933 | 0.000 E − 00 |
| 2 | 1.94 | −1.94 | 1.94 | −1.94 | 0.000 E − 00 |
| 1 | 4.95 | −4.95 | 4.95 | −4.95 | 0.000 E − 00 |

EXAMPLE II

An Amberlyst 15 hydrolysis catalyst was evaluated in a laboratory unit.

The laboratory unit was made up of a stainless steel column, 1 inch in diameter and 24 inches in length. This column contained the catalyst bed. The gas comprising methyl acetate in nitrogen was fed into the bottom of the column, while liquid water was fed through the top. The inlet gas flow was controlled by a Brooks flow controller, while water flow was controlled by a Milton Roy pump. Each of the lines through which the methyl acetate and water were passed into the column was heated by a 1,000-watt cartridge heater. Temperatures were measured at the gas feed inlet, the liquid water inlet, and the column skin. During a typical run, feed gas samples were taken at the beginning, middle, and end of the run, vent gas samples were taken every 15 minutes, and total liquid effluent was analyzed at the conclusion of the run. Each of the runs was two hours in length. The vent gas concentrations stabilized in approximately 45 minutes.

Several runs were carried out in the above-described equipment. In order to eliminate pressure-drop problems, some of the catalyst beads were supported on flexible window screens, silicon adhesive diluted in acetic acid being employed as glue to hold the beads in place, and two six-inch square screens were rolled around inert spacers and loaded into the column, the screens containing 20 grams of dry catalyst, and two inches of ceramic saddles were put on top of the screen (to help disperse the water feed).

Two runs were made without catalyst. In one, Run No. 1, approximately six inches of ceramic saddles were used in the place of catalyst. In the other, Run No. 2, window screen was employed. The purpose was to ascertain how much hydrolysis occurred in the absence of catalyst and how much methyl acetate was absorbed into the water.

Three runs were conducted with Amberlyst 15 being the catalyst. Run No. 3 employed screens having Amberlyst 15 supported on them. The screens were rolled around an inert spacer. The height of the screens was approximately 12 inches and they contained approximately 20 gm (dry weight) of catalyst. Approximately 2 inches of the ceramic saddles were placed on top of the screens to aid in water dispersion.

These runs were made with gas flow rates of 1.07 standard cubic feet per hour (SCFH), 0.20 SCFH, or 0.13 SCFH. The data obtained from these tests are presented hereinafter in Table II.

TABLE II

RESULTS OF ADSORPTION/HYDROLYSIS TESTS - CONVERSION OF METHYL ACETATE TO ACETIC ACID AND METHANOL

| Run No. | 1 | 2 | 3 | 4 | 5 |
|---|---|---|---|---|---|
| Catalyst | saddles | screens | catalyst | catalyst | catalyst |
| Feed gas flow, SCFH | 1.07[a] | 1.07 | 1.07 | 0.20 | 0.13 |
| Water feed rate, ml/hr | 70 | 70 | 70 | 70 | 70 |

TABLE II-continued
RESULTS OF ADSORPTION/HYDROLYSIS TESTS - CONVERSION OF METHYL ACETATE TO ACETIC ACID AND METHANOL

| Run No. | 1 | 2 | 3 | 4 | 5 |
|---|---|---|---|---|---|
| Liquid inlet temp. °F. | 173 | 166 | 170 | 145[d] | 181 |
| °C. | 79 | 75 | 77 | 63 | 83 |
| Run time, min | 120 | 120 | 120 | 120 | 120 |
| Feed gas comp. vol % | | | | | |
| Methyl acetate | 2.0 | 1.69 | 1.54 | 1.60 | 1.52 |
| Methanol | — | 0.006 | 0.006 | 0.007 | 0.004 |
| Acetic acid | — | 0.006 | 0.004 | — | 0.002 |
| Exit gas comp. avg. vol %[b] | | | | | |
| Methyl acetate | 1.0 | 1.6 | 1.35 | 1.4 | 0.65 |
|  | (0.22) | (0.12) | (0.046) | (0.12) | (0.082) |
| Methanol | 0.012 | 0.006 | 0.18 | 0.28 | 0.14 |
|  | (0.009) | (0.002) | (0.069) | (0.095) | (0.052) |
| Acetic acid | 0.004 | — | 0.01 | 0.008 | 0.005 |
|  | (0.008) |  | (0.01) | (0.005) | (0.005) |
| Liquid effluent comp. wt % | | | | | |
| Methyl acetate | 0.778 | 0.248 | 0.417 | 0.145 | 0.096 |
| Methanol | 0.010 | 0.004 | 0.060 | 0.062 | 0.041 |
| Acetic acid | 0.024 | trace | 0.231 | 0.326 | 0.108 |
| Total moles fed | | | | | |
| Methyl acetate | 0.046 | 0.046 | 0.042 | 0.0081 | 0.0049 |
| Methanol | — | 0.00016 | 0.00016 | 0.000035 | 0.000014 |
| Acetic acid | — | neg | 0.00011 | neg | 0.000007 |
| Total moles out | | | | | |
| Methyl acetate | 0.036 | 0.048 | 0.044 | 0.0096 | 0.0034 |
| Methanol | 0.0007 | 0.00034 | 0.0074 | 0.0039 | 0.0021 |
| Acetic acid | 0.0006 | neg | 0.0052 | 0.0071 | 0.0025 |
| Material balance, % | 80 | 105 | 119 | 254 | 116 |
| Methyl acetate Conv, %[c] | 2 | <1 | 13(15) | — | 31(40) |
| Percent in liquid | | | | | |
| Methyl acetate | 40 | 9 | 18 | — | 52 |
| Methanol | 60 | 49 | 32 | — | 83 |
| Acetic acid | 100 | — | 96 | — | 100 |

[a] Near the end of the run, the flow rate decreased because the feed tank was running out of gas.
[b] Average of the readings during the run with standard deviation in parentheses. In terms of calculating the amounts of gas products formed, all of the readings (not the average) were used.
[c] The first number is based on the total moles out. The number in parentheses is based on moles fed.
[d] The liquid preheater broke down during this run, resulting in loss of temperature control for the inlet water.

EXAMPLE III

An Amberlyst 15-on-ceramic saddles catalyst was evaluated in the laboratory unit described hereinabove in Example II.

A determination of the hydrolysis resulting from the ceramic saddles was conducted. In this test. Run No 6, the reactor column was loaded with 123 gm of the ceramic saddles. The column was heated to 94° C. (202° F.) and the water inlet to 77° C. (170° F.). Water was pumped into the top of the column at a rate of 70 ml/hr. Methyl acetate in nitrogen (1.6 vol % methyl acetate) was introduced into the bottom of the column at a rate of 1.1 SCFH. This gas mixture also contained traces of methanol (0.0035 vol %) and acetic acid (0.004 vol %). The reaction system was stabilized after 30 to 45 minutes and the reaction was run for two hours while concentrations of methyl acetate, methanol, and acetic acid in the effluent gas were monitored during the run. The liquid bottoms and the condensed liquid overhead were analyzed after the run. Acetic acid was found in the effluent gas at a level that was similar to that in the feed gas ($\leq$0.004 vol %). Acetic acid was not found in the liquid samples. Based upon the amount of methanol found in the liquid samples and effluent gas, the amount of methyl acetate that was hydrolyzed was 2.2 mole % of the total methyl acetate that was fed to the unit. The methyl acetate that could be accounted for after the completion of the run as unreacted methyl acetate, acetic acid, and methanol amounted to 93 mole % of the methyl acetate fed.

In Run No 7, the reaction conditions were the same as those described in Run No 6, except that the catalyst was made up of approximately 23 gm of Amberlyst 15 supported on the ceramic saddles. Concentrations of methyl acetate, acetic acid, and methanol in the feed gas averaged 1.8 vol %, 0.024 vol %, and 0.033 vol %, respectively. The reaction was stopped after 2 hr. The amount of methyl acetate that was hydrolyzed was found to be 14 mole % of the methyl acetate fed. This was based upon the amount of acetic acid and methanol formed in the liquid samples and effluent gas minus the amounts of acetic acid and methanol in the feed gas. Ninety percent of the acetic acid present was in the bottoms flask, while 78% of the methyl acetate and methanol had gone overhead. The accountability of the methyl acetate that was fed was 86 mole %.

In Run No 8, the reaction conditions were the same as those described in Run No 6 and Run No 7, except that water was introduced at twice the flow rate and the liquid (water) inlet temperature was 98° C. (208° F.). The catalyst from Run No 7 was used. The concentrations of methyl acetate, acetic acid, and methanol in the feed gas averaged 1.8 vol %, 0.002 vol %, and 0.035 vol %, respectively. The reaction was stopped after 2 hr. Based upon the amounts of methanol and acetic acid produced during the reaction, the amount of methyl acetate that was hydrolyzed was 20%. Ninety-seven percent of the acetic acid present was in the bottoms while 67% and 47% of the methyl acetate and methanol, respectively, had gone overhead. The accountability of methyl acetate was 85% of the methyl acetate fed.

In Run No 9, the reaction conditions were the same as those described in Runs Nos 6 and 7, except that the flow rate of the feed gas was 0.21 SCFH. The catalyst from Runs Nos 7 and 8 was used in this run. The average concentrations of methyl acetate and methanol in the feed gas were 1.9 vol % and 0.036 vol %, respectively. No acetic acid was detected in the feed gas. The reaction was run for 2 hrs. Based upon the amounts of methanol and acetic acid produced, 34% of the methyl acetate that was fed was hydrolyzed. Ninety-seven percent of the acetic acid present was in the bottoms, while 30% and 29% of the methyl acetate and methanol, respectively, were found in the overhead. The methyl acetate accountability as unreacted methyl acetate, acetic acid, and methanol after the run was stopped was 101% of the methyl acetate fed.

The results of these tests demonstrate that hydrolysis of the methyl acetate does occur in catalyzed runs while only a small amount (up to 2%) of hydrolysis occurs in noncatalyzed runs. Partial separation is achieved concurrently to the hydrolysis. Absorption data indicate that the unit has less than one theoretical stage. Six stages are predicted to be necessary for high conversion and separation efficiency.

EXAMPLE IV

The apparatus employed in this run, Run No 10, comprised a column connected to a 3-neck flask. A condensor was connected to the column at a point near the top of the column. The flask served as a boiler and was encased by a Variac heater. The column contained 10.2 gm of catalyst, i.e., catalyst-packing material, in a tube that was 12.7 mm in inside diameter. The catalyst bed, made up of three equivalent sections, was 15.6 cm in height. The catalyst volume was 19.8 cu cm. Nitrogen was slowly added to the column at a point above the catalyst bed for pressure control. A furnace surrounded the column at the location of the catalyst bed. The boiler was maintained at a temperature of 100° C. (212° F.) and the catalyst bed was maintained at a temperature of 112° C. (234° F.). The portion of the column above the catalyst bed was not insulated. The uninsulated section provided a large amount of reflux to the catalyst.

A volumetric funnel and stopcock were located between the bottom of the condenser and the three-neck flask.

The vapors that escaped the column were primarily methyl acetate. They were condensed and returned through the volumetric funnel and stopcock to the three-neck flask.

A 10.2-gm portion of catalyst comprising silicalite coated on cordierite honeycombs and obtained from Corning Company (Corning Code 9475) was charged to the column.

Initially, a feed comprising 35 ml of methyl acetate and 100 ml of water was charged to the flask. Methyl acetate was added continuously to the flask at a rate of 0.14 ml per min for the first 90 minutes and then at a rate of 0.1 ml per min up until the 280-minute point in time.

Initially, the selectivity to acetic acid was zero, while the selectivity to acetone was 100%. After two hours, the selectivity to acetic acid was 60%; after three hours, 86%; after six hours, 97.6% at 98.7% conversion; and after nine hours, 99.2% at 99.2% conversion. By that time, selectivity to acetone was only 0.8% and the catalyst was lined out in the high acetic acid selectivity mode.

Accordingly, Run No 10 illustrates the very high acetic acid selectivities that can be achieved after the catalyst has been lined out. The acetic acid selectivity became very high after a reasonably short time.

EXAMPLE V

Methyl acetate was hydrolyzed to methanol and acetic acid in Run No 11.

The apparatus employed in this run was made up of a column connected to a U-bend tube inserted in a heated water pool, which simulated a reboiler. A catalyst bed, similar to that described in Example IV, was located in the column. A condenser was mounted above the column, so that all reflux was returned to the catalyst zone.

A 10.2-gm portion of catalyst was charged to the column. The catalyst comprised silicalite coated on cordierite honeycombs obtained from Corning Company (Corning Code 9475). The methyl acetate and water were introduced into the system above the reaction zone in a ratio of 1.1:1. The methyl acetate was pumped at a rate of 0.0488 ml/min (0.00089 gm-moles/min), while the water was pumped at a rate of 0.0176 ml/min (0.00098 gm-moles/min).

The data obtained from Run No 11 are presented hereinbelow in Table III.

TABLE III

| METHYL ACETATE CONVERSION | | | | | | |
|---|---|---|---|---|---|---|
| | | % Selectivity to | | | Temp., °C. | |
| Time, min | Conversion % | Acetic acid | Acetone | Other | Reaction | Highest |
| 40 | 8.9 | 99.8 | 0.0 | 0.2 | 187 | 187 |
| 80 | 25.8 | 98.2 | 0.99 | 0.81 | 194 | 200 |
| 120 | 22.9 | 99.2 | 0.0 | 0.82 | 140 | 171 |
| 160 | 29.8 | 88.7 | 9.5 | 1.79 | 167 | 221 |
| 200 | 25.0 | 95.0 | 3.3 | 1.73 | 204 | 218 |
| 240 | 27.9 | 88.6 | 5.5 | 1.31 | 172 | 204 |
| 280 | 26.6 | 91.0 | 6.3 | 2.62 | 157 | 212 |
| 320 | 28.4 | 91.2 | 6.3 | 2.48 | 171 | 171 |
| 360 | 24.0 | 98.0 | 0.9 | 1.06 | 130 | — |
| 400 | 30.4 | 88.9 | 8.8 | 2.31 | 182 | — |
| 440 | 32.0 | 78.7 | 17.4 | 3.92 | 190 | 214.5 |

In this particular run, the conversions were normally between 25% and 32%. The selectivities to acetic acid were high. However, the selectivities to acetone were greater than desired. The reaction seemed to be more selective to acetic acid at lower temperatures. The high acetone levels were due probably to the higher ratio of methyl acetate to water. Increased water levels will probably result in lower selectivities to acetone.

The above examples demonstrate that the processes of the present invention employing catalytic distillation provide a suitable means for converting methyl acetate to acetic acid.

What is claimed is:

1. A process for recovering acetic acid from methyl acetate, by hydrolyzing said methyl acetate to acetic acid and methanol and simultaneously separating said acetic acid and said methanol, which process comprises contacting counter-currently in a separation column a stream comprising methyl acetate with water in the presence of a catalyst-packing material comprising a hydrolysis catalyst to produce less volatile acetic acid and more volatile methanol, separating said acetic acid from said methanol in said separation column by said volatility, said acetic acid being withdrawn from said separation column as a bottoms stream, said methanol being carried up and out of said separation column, said contacting and said separating being carried out coextensively in said column, and recovering said acetic acid.

2. The process of claim 1, wherein said hydrolysis catalyst is an acidic cation exchange resin.

3. The process of claim 1, wherein said stream comprising methyl acetate is obtained as a by-product in a process for the partial oxidation of a polymethylbenzene to the corresponding aromatic polycarboxylic acid in the presence of an oxidation catalyst and a solvent comprising acetic acid.

4. The process of claim 1, wherein said contacting is carried out at a pressure within the range of about 1.3 psia (8.96 kPa) to about 600 psia (4.137 kPa) and a liquid volumetric hourly space velocity within the range of about 0.1 hr$^{-1}$ to about 10 hr$^{-1}$.

5. The process of claim 2, wherein said stream comprising methyl acetate is obtained as a by-product in a process for the partial oxidation of a polymethylbenzene to the corresponding aromatic polycarboxylic acid in the presence of an oxidation catalyst and a solvent comprising acetic acid.

6. The process of claim 2, wherein said acidic cation exchange resin comprises a sulfonated polystyrene with divinyl benzene crosslinking.

7. The process of claim 3, wherein para-xylene is said polymethylbenzene and terephthalic acid is said polycarboxylic acid.

8. The process of claim 5, wherein para-xylene is said polymethylbenzene and terephthalic acid is said polycarboxylic acid.

9. The process of claim 7, wherein said separation column is the acetic acid dehydration tower employed in said process for the partial oxidation of para-xylene to terephthalic acid.

10. The process of claim 8, wherein said separation column is the acetic acid dehydration tower employed in said process for the partial oxidation of para-xylene to terephthalic acid.

11. The process of claim 8, wherein said acidic cation exchange resin comprises a sulfonated polystyrene with divinyl benzene crosslinking.

12. The process of claim 8, wherein said contacting is carried out at a pressure within the range of about 1.3 psia (8.96 kPa) to about 600 psia (4,137 kPa) and a liquid volumetric hourly space velocity within the range of about 0.1 hr$^{-1}$ to about 10 hr$^{-1}$.

13. The process of claim 10, wherein said acidic cation exchange resin comprises a sulfonated polystyrene with divinyl benzene crosslinking.

14. A process of partial oxidation of a polymethylbenzene to the corresponding aromatic polycarboxylic acid, which process comprises contacting a feed comprising said polymethylbenzene with molecular oxygen in a reaction zone in the presence of an oxidation catalyst and a solvent comprising acetic acid to produce said polycarboxylic acid and at least a small amount of methyl acetate, withdrawing from said reaction zone said polycarboxylic acid and a first stream comprising said methyl acetate, water, and acetic acid, introducing said first stream into a dehydration column wherein a second stream comprising water and methyl acetate is separated from a third stream comprising acetic acid, contacting counter-currently said second stream comprising methyl acetate with water in a separation column containing a catalyst-packing material comprising a hydrolysis catalyst to hydrolyze said methyl acetate into more volatile methanol and less volatile acetic acid product, and simultaneously separating said methanol from said acetic acid product in said separation column by said volatility, said acetic acid product being withdrawn from said separation column as a bottoms stream, said methanol being carried up and out of said separation column, said contacting and said separating being carried out coextensively in said separation column, and returning at least a large portion of said acetic acid product to said reaction zone.

15. The process of claim 14, wherein said polymethylbenzene is para-xylene and said polycarboxylic acid is terephthalic acid.

16. The process of claim 14, wherein said separation column is operated at a pressure within the range of about 1.3 psia (8.96 kPa) to about 600 psia (4,137 kPa) and a liquid volumetric hourly space velocity within the range of about 0.1 hr$^{-1}$ to about 10 hr$^{-1}$.

17. The process of claim 14, wherein said hydrolysis catalyst comprises an acidic cation exchange resin.

18. The process of claim 14, wherein said polymethylbenze is paraxylene and said polycarboxylic acid is terephthalic acid.

19. The process of claim 14, wherein said hydrolysis catalyst comprises an acidic cation exchange resin.

20. The process of claim 15, wherein said separation column is operated at a pressure within the range of about 1.3 psia (8.96 kPa) to about 600 psia (4,137 kPa) and a liquid volumetric hourly space velocity within the range of about 0.1 hr$^{-1}$ to about 10 hr$^{-1}$.

21. The process of claim 16, wherein said hydrolysis catalyst comprises an acidic cation exchange resin.

22. The process of claim 18, wherein said acidic cation exchange resin comprises a sulfonated polystyrene with divinyl benzene crosslinking.

23. The process of claim 18, wherein said separation column is operated at a pressure within the range of about 1.3 psia (8.96 kPa) to about 600 psia (4,137 kPa) and a liquid volumetric hourly space velocity within the range of about 0.1 hr$^{-1}$ to about 10 hr$^{-1}$.

24. The process of claim 23, wherein said hydrolysis catalyst comprises an acidic cation exchange resin.

25. The process of claim 24, wherein said acidic cation exchange resin comprises a sulfonated polystyrene with divinyl benzene crosslinking.

26. In an improved process for the partial oxidation of a polymethylbenzene to the corresponding aromatic polycarboxylic acid wherein said polymethylbenzene is oxidized with molecular oxygen in the presence of an oxidation catalyst and a solvent comprising acetic acid to produce said polycarboxylic acid and, as a by-product, at least a small amount of methyl acetate, the improvement which comprises contacting counter-currently a stream comprising said methyl acetate with water in a separation column containing a hydrolysis catalyst to convert said methyl acetate into a less volatile acetic acid product and more volatile methanol and simultaneously separating said methanol from said acetic acid product by said volatility, said acetic acid product being withdrawn from said separation column as a bottoms stream, said methanol being carried up and out of said separation column, said contacting and said separating being carried out coextensively in said separation column, and recovering at least a large portion of said acetic acid product.

27. The improved process of claim 26, wherein said process uses a dehydration column to remove water from acetic acid and said dehydration column is used as said separation column.

28. The improved process of claim 26, wherein said hydrolysis catalyst is an acidic cation exchange resin.

29. The improved process of claim 27, wherein said hydrolysis catalyst is an acidic cation exchange resin.

30. In an improved process for the partial oxidation of para-xylene to terephthalic acid wherein said para-xylene is oxidized with molecular oxygen in the presence of an oxidation catalyst and a solvent comprising acetic acid to produce said terephthalic acid and, as a by-product, at least a small amount of methyl acetate, the improvement which comprises contacting a stream comprising said methyl acetate with water in a separation column containing a a catalyst-packing material comprising a hydrolysis catalyst to convert said methyl acetate into an acetic acid product and methanol and separating said methanol from said acetic acid product, said contacting and said separating being carried out coextensively in said separation column, and recovering at least a large portion of said acetic acid product.

31. The improved process of claim 30, wherein said separation column is operated at a pressure within the range of about 1.3 psia (8.96 kPa) to about 600 psia (4,137 kPa) and a liquid volumetric hourly space velocity within the range of about 0.1 hr$^{-1}$ to about 10 hr$^{-1}$.

32. The improved process of claim 30, wherein said hydrolysis catalyst is an acidic cation exchange resin.

33. This improved process of claim 31, wherein said separation column is operated at a pressure within the range of atmospheric to about 150 psia (1,034 kPa) and a liquid volumetric hourly space velocity within the range of about 0.5 hr$^{-1}$ to about 5 hr$^{-1}$.

34. The improved process of claim 30, wherein said separation column is operated at a pressure within the range of about 1.3 psia (8.96 kPa) to about 600 psia (4,137 kPa) and a liquid volumetric hourly space velocity within the range of about 0.1 hr$^{-1}$ to about 10 hr$^{-1}$.

35. The improved process of claim 30, wherein said hydrolysis catalyst is an acidic cation exchange resin.

36. The improved process of claim 32, wherein said acidic cation exchange resin comprises a sulfonated polystyrene with divinyl benzene crosslinking.

37. The improved process of claim 34, wherein said hydrolysis catalyst is an acidic cation exchange resin.

38. The improved process of claim 35, wherein said acidic cation exchange resin comprises a sulfonated polystyrene with divinyl benzene crosslinking.

39. The improved process of claim 37, wherein said acidic cation exchange resin comprises a sulfonated polystyrene with divinyl benzene crosslinking.

40. The improved process of claim 39, wherein said separation column is operated at a pressure within the range of atmospheric to about 150 psia (1,034 kPa) and a liquid volumetric hourly space velocity within the range of about 0.5 hr$^{-1}$ to about 5 hr$^{-1}$.

* * * * *

UNITED STATES PATENT OFFICE
CERTIFICATE OF CORRECTION

Patent No. 5,113,015   Dated May 12, 1992

Inventor(s) David A. Palmer, Keith D. Larson and Kristi A. Fjare

It is certified that error appears in the above-identified patent and that said Letters Patent is hereby corrected as shown below:

| Col. | Line | |
|---|---|---|
| 19 | 14 | "600 psia (4.137 kPa)" should read --600 psia (4,137 kPa)-- |

Signed and Sealed this

Sixth Day of July, 1993

Attest:

MICHAEL K. KIRK

Attesting Officer   Acting Commissioner of Patents and Trademarks